(12) United States Patent
Laurie

(10) Patent No.: US 6,579,830 B1
(45) Date of Patent: Jun. 17, 2003

(54) METHOD OF MISTLETOE CONTROL

(76) Inventor: Gavin Laurie, 1575 Moultrie Hwy., Quitman, GA (US) 31643

( * ) Notice: Subject to any disclaimer, the term of this patent is extended or adjusted under 35 U.S.C. 154(b) by 0 days.

(21) Appl. No.: 10/223,380

(22) Filed: Aug. 20, 2002

(51) Int. Cl.[7] .................. A01N 25/00; A01N 65/02; A01G 13/00
(52) U.S. Cl. .................. 504/116.1; 504/357; 504/362; 47/DIG. 11
(58) Field of Search .............. 504/116.1, 357, 504/362; 47/DIG. 11

(56) References Cited

U.S. PATENT DOCUMENTS

| | | | | |
|---|---|---|---|---|
| 1,949,799 A | | 3/1934 | Knight | 167/43 |
| 2,160,929 A | * | 6/1939 | Warner et al. | 167/45 |
| 2,554,192 A | | 5/1951 | Byer | 71/2.3 |
| 3,063,821 A | | 11/1962 | Weil | 71/2.3 |
| 3,227,609 A | | 1/1966 | Wilson, Jr. | 167/28 |
| 5,429,646 A | * | 7/1995 | Givens | 47/58 |
| 5,814,325 A | | 9/1998 | Rod | 424/407 |

OTHER PUBLICATIONS

USDA Agricultural Handbook 709, Chapter 13, "Control". 1996.*

Schmitt, Craig L. USDA Publication BMZ–96–07, "Management of Ponderosa Pine Infected with Western Dwarf Mistletoe in Northeastern Oregon". Apr. 1996.*

Arnold, Charles. "Homeowner's Guide: Dwarf Mistletoe Management". Feb. 1998. (http://www.rms.nau.edu/mistletoe/hguide/hguide).*

* cited by examiner

Primary Examiner—S. Mark Clardy
(74) Attorney, Agent, or Firm—Dowell & Dowell, P.C.

(57) ABSTRACT

A method for destroying mistletoe by the application of barrier coatings, such as natural oils, to cover the surfaces of a mistletoe plant to block stomatal openings during a dormant period of a host tree affected by the mistletoe so that the mistletoe is effectively deprived of all nutrients.

9 Claims, No Drawings

METHOD OF MISTLETOE CONTROL

BACKGROUND OF THE INVENTION

1. Field of the Invention

This invention is generally directed to methods for controlling growth of parasitic plants and more particularly to a method for destroying mistletoe using oils without causing harm to host trees affected by the mistletoe and without adverse affect to the environment.

2. Brief Description of the Related Art

Mistletoe is a parasitic plant that grows on conifers, hardwoods, ornamental trees, fruit trees and the like. Mistletoe robs nutrients and water from the host plant as well as produces its own additional nutrients in the same manner as other plants. There are two species of mistletoe in North America. Arceuthobium sp is a dwarf mistletoe that affects conifers in the Western United States. *Phoradendron flavescens* is a true or leafy mistletoe which affects trees in warmer climatic regions of the United States. Both species are known to cause major economic damage and can effect trees of any age or size. When a tree becomes a host to the mistletoe, if the mistletoe is allowed to flourish, the growth of the tree can be stunted and fruit and nut production seriously affected. In some cases, the mistletoe actually destroys the host tree.

There is currently no labeled chemical for control of mistletoe. Current procedures for controlling mistletoe involve pruning affected limbs of the host tree. Such pruning is a very costly and time consuming process and therefore is not economically feasible or practical in areas of heavy infestation.

In view of the foregoing, there is a need to provide a process or method to effectively control or destroy parasitic plants such as mistletoe over large expanses of acreage in a cost effective manner without adverse affect to the host plant and to the surrounding environment.

Although it has been known to control weeds and other plants by the use of oils as herbicides to terminate plant growth, it has not been known to use oils in a method nor at a time of dormancy of a host tree in order to effectively destroy mistletoe without adverse affect on the host plant and the environment.

In U.S. Pat. No. 3,063,821 to Weil, mineral oil mixtures are used to control weeds. In U.S. Pat. No. 2,554,192 to Puente et al., oils are used as herbicides. In U.S. No. Pat. 2,160,929 to Warner et al., mineral oils are used to kill plants.

SUMMARY OF THE INVENTION

The present invention is directed to a method of destroying mistletoe which does not adversely affect host plants and trees by the application of a physical barrier to the surface of the mistletoe plant which is applied, such as by spray application, during a dormancy period of the host tree or plant. In accordance with the invention, complete surface coverage of the mistletoe plant is promoted during the dormancy period of a host as there is reduced foliage which could otherwise block the application of the physical barrier which, in the preferred embodiment, is by way of an oil which is sprayed on the surface of the mistletoe. The oil blocks the stomatal openings and thereby interrupts the intake of carbon dioxide and water to the mistletoe which causes a shutdown of the metabolic process. In accordance with the process, when the host plant is dormant, it is not furnishing any nutrients to the parasitic plant. The lack of nutrients from the host plant timed together with the interruption of the intake of carbon dioxide and water to the mistletoe facilitates the destruction of the mistletoe.

The oils used as a physical coating or barrier in accordance with the process includes those which are readily available on the market including natural unrefined oils such as vegetable oils. The oils must be applied in sufficient strength and must have sufficient viscosity to create physical barriers that will not be washed from the surface of the mistletoe during snow, heavy dew, or rainfall as the time required for destruction of the mistletoe may extend several months in duration. Thus, the surface coating either must be maintained or reapplied during this period.

It is a primary object of the present invention to provide a process which effectively destroys mistletoe with minimal harm to a host tree and its fruit or nuts and which is completely safe to the environment and not harmful to individuals using the process.

DESCRIPTION OF THE PREFERRED EMBODIMENT

As a parasitic plant, mistletoe receives nutrition from sapping nutrients from a host tree. Mistletoe also undertakes nutrient production through photosynthesis by the intake of carbon dioxide and water, as do other plants. In accordance with the process of the present invention, a coating is applied to the surface of the mistletoe in order to interrupt the ability of the mistletoe to create its own nutrients by prohibiting photosynthesis by interruption of intake of carbon dioxide and water. This interruption to the creation of nutrients by the mistletoe is coincided with a dormancy of the host tree from which the mistletoe receives parasitic nutrients. By timing the application of the barrier coatings of the mistletoe at a time when nutrients cannot be obtained from the host, the mistletoe cannot receive or create enough nutrients and water to survive.

In accordance with the process, a spray application is made, during the dormancy period of the host tree, that gives a complete surface coverage to the mistletoe plant. This complete coverage is preferably provided by the application of readily available and low cost oils such as natural unrefined oils including various vegetable oils. Other oil products which are environmentally compatible may also be used in accordance with the teachings of the present invention.

When selection is made of a coating material, such as oil, the material must have sufficient strength and viscosity to create a physical barrier coating the surface of the mistletoe plant, which barrier will not be removed for a period of several months by environmental conditions such as heavy dews, snow, or rainfall.

During testing, readily available products on the market, such as superior oil, and crop oil, were used as barrier coatings. However, these oils are emulsions and are of a lesser viscosity than natural unrefined oils, and when applied do not provide the extended coverage necessary to withstand being washed off by forms of precipitation. They are also not environmentally friendly.

It was found that natural unrefined oils, such as vegetable oil, when applied in sufficient amounts to provide complete coverage, form an impenetrable barrier that withstands weather and time. The added advantage of using natural oils is that they are biodegradable and environmentally friendly to the host plant and safe to the user.

However, this invention is not limited to the use of oil. Any product which is used during dormancy, that will form an impenetrable barrier coating, is biodegradable, and will stay on the mistletoe plant long enough to stop the metabolic process, will work. The ultimate destruction of the mistletoe can be a very slow process extending from two months to six months depending upon the size of the individual parasitic plant.

In order to destroy mistletoe, it is necessary to completely envelope the plant's entire surface, both leaf and stem, with oil. The spraying of oil can be accomplished in many different ways. During test trials, two readily available methods were used. The first was the use of a regular engine driven, tractor pulled, pecan sprayer. The other employed the use of a 45-foot mobile hoist with platform for the operator, utilizing a 120-gallon, tractor operator, herbicide-pesticide sprayer, connected to a 50-foot rubber pressure hose with hand-operated spray gun. Both methods of spraying killed the mistletoe. However, the platform operation was more effective because the spray was concentrated.

Rate of barrier coating application depends upon a number of variables: the viscosity and consistency of the oil, the size of the tree, the degree of mistletoe infestation and the type of equipment used in the spray application. Weather conditions such as moisture and wind play an important part in the process. Excessive wind will scatter the spray while the mistletoe leaves must be dry in order for the oil to adhere. The spray application must cover the entire plant.

Two test plots were used. The first consisted of mature, 25-inch to 35-inch diameter trees interspaced with a few 18-year old trees. Adjacent to it were a plot of 16-year old transplanted trees, and a plot of new 7-year old trees. The larger trees were very heavily infested with mistletoe, with from 20 percent to 70 percent coverage. During dormancy, some to the trees had the appearance of evergreens. The younger trees were lightly infected, with from one to twelve clusters.

The regular pecan sprayer was initially used on the larger trees. Spraying was accomplished at dusk, during dry weather, when the air movement was less than three miles per hour. The sprayer was operated at an engine rpm that permitted the oil spray to reach the tops of the largest trees, which were 70 to 100-feet tall.

Various rates of ground speed were tried. The most successful was operating at from one to one and a half mph.

Subsequently, the self-propelled platform with tractor operated pesticide sprayer was used. These tests were performed during daylight hours, dry weather conditions, and a variable wind speed of up to 10 miles per hour. A separate tractor carried a PTO, power-take-off, operated regular pesticide-herbicide sprayer. By disconnecting the central spray arm and nozzles and inserting a 50-foot rubber pressure hose to the central port of the control valve, it was possible to operate a variable orifice spray gun. The pressure to the operator varied from 80 to 100 PSI. As there was a breeze, the operation was conducted up-wind and only a portion of the tree could be covered. This method thoroughly soaked the mistletoe, and in most trees, greater than 95 percent of the parasitic plants were destroyed in one spraying.

On the mid-sized trees, the pecan sprayer was not utilized, as too much material would have been wasted by the broadcast application. The self-propelled platform produced excellent results with a much lower volume of oil being used. On the smaller trees, up to approximately 25 feet in height, it was not necessary to use the mobile platform, as the tractor sprayer with pump could reach the infestation. Spraying when mistletoe infestations are small in size and quantity can save many dollars rather than spraying later.

The process of spraying oil on the mistletoe does not produce a rapid destruction of this parasitic plant. The first indication that the play is dying is the shedding of leaves. This can occur anytime after five days. In one to two months the leaves will have either shed or be darkened and the stems will become brittle and begin to snap off at the joints. Death of the plant generally occurs after three months. It may take years before the plant finally breaks off entirely. Generally, the host branches are not affected by the death of the mistletoe plant on lightly infected trees; however, when there is a heavy infestation some of the branches of the host may die.

A further advantage of the process of the present invention is that by timing the application of the oil to the surface of the mistletoe during the dormancy period of the host plant, the normal foliage of the host plant does not interfere with the spray application to the mistletoe. Again, the amount of oil or barrier coating will vary depending upon the size of the mistletoe plant being controlled, however, sufficient coating is applied to the plant in order to block the stomatal openings of the plant and thereby interrupt the intake of carbon dioxide and water.

In some instances and especially where mistletoe is well established, it may be necessary to apply repeat coatings to the mistletoe during the dormancy period of the host plant in order to ensure that effective coating is retained on the surface of the mistletoe plant to prevent the intake of carbon dioxide and water.

Thus, in accordance with the invention, it is possible to effectively control and destroy mistletoe which is affecting host trees and other plants during the dormancy period of the host tree or plant by the application of surface coatings, such as natural oils, to the mistletoe. As the process uses oils and other coatings which are fully environmentally compatible, there is no environmental damage caused by the process to surrounding vegetation and soil.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

I claim:

1. A process for controlling mistletoe which has infested a host plant comprising the steps of: during a dormancy period of the host plant applying a surface coating of an environmentally compatible material to the mistletoe so as to effectively block the stomatal openings of the mistletoe to thereby interrupt the intake of carbon dioxide and water.

2. The process of claim 1 including the additional step of applying a subsequent surface coating of the environmentally compatible material to the mistletoe plant in a period of time spaced from an initial application in order to maintain a coating on the mistletoe plant to interrupt the intake of carbon dioxide and water during the dormancy of the host plant.

3. The process of claim 2 wherein the environmentally compatible material is selected from a group of natural oils having viscosity sufficient to create a physical barrier on the mistletoe plant which will not be removed over a period of at least thirty days by environmental conditions including snow, dew or rainfall.

4. The process of claim 3 wherein the oil is a vegetable oil.

5. The process of claim 1 wherein the environmentally compatible material is selected from a group of natural oils having viscosity sufficient to create a physical barrier on the mistletoe plant which will not be removed over a period of at least thirty days by environmental conditions including snow, dew or rainfall.

6. The process of claim 5 wherein the oil is a vegetable oil.

7. The process of claim 6 wherein the vegetable oil applied when the mistletoe is dry.

8. The process of claim 1 wherein the environmentally compatible material is vegetable oil.

9. The process of claim 8 wherein the vegetable oil applied when the mistletoe is dry.

* * * * *